United States Patent
Knobler

(10) Patent No.: US 9,616,123 B1
(45) Date of Patent: Apr. 11, 2017

(54) METHOD AND COMPOUND FOR TREATMENT OF MENOPAUSAL SYMPTOMS

(76) Inventor: Robert L. Knobler, Fort Washington, PA (US)

( * ) Notice: Subject to any disclaimer, the term of this patent is extended or adjusted under 35 U.S.C. 154(b) by 349 days.

(21) Appl. No.: 13/411,660

(22) Filed: Mar. 5, 2012

(51) Int. Cl.

| | |
|---|---|
| *A61K 31/433* | (2006.01) |
| *A61K 31/404* | (2006.01) |
| *C07D 209/34* | (2006.01) |
| *C07D 285/10* | (2006.01) |
| *A61P 15/00* | (2006.01) |
| *A61K 45/06* | (2006.01) |
| *A61K 31/4168* | (2006.01) |
| *A61K 31/415* | (2006.01) |

(52) U.S. Cl.
CPC ............ *A61K 45/06* (2013.01); *A61K 31/415* (2013.01); *A61K 31/4168* (2013.01)

(58) Field of Classification Search
CPC .. A61K 45/06; A61K 31/415; A61K 31/4168; A61K 31/433; A61K 31/4045; A61K 31/445
See application file for complete search history.

(56) References Cited

U.S. PATENT DOCUMENTS

2010/0298305 A1* 11/2010 Capehart ...................... 514/221

OTHER PUBLICATIONS

Trenkwalder et al. in J Neural Neurosurg Psychiatry 2004; 75:92-97.*
Smith et al. in the American Journal of Hospice & Palliative Care, 17(1), 50-58 (2000).*
'Tablet definition' in www.google.com/search?q=tablet+definition & sourceid=ie7&rls=com.microsoft:en-us:IE-Address& ie=&oe= (retrieved from the internet on Jul. 30, 2013).*
Soares et al. in Obstetrics and Gynecology 108(6), 1402-1410 (2006).*
Najib in Clinical Therapuetics, 28(4):491-516 (2006) (Abstract).*
Korczyn et al. in Movement Disorders 31(1), 46-51 (1998).*
Zichella et al. in Maturitas 8, 229-237 (1986).*
DeFronzo Dobkin et al. in Menopause Int. 15(1): 13-18 (2009).*

* cited by examiner

*Primary Examiner* — Dennis Heyer
(74) *Attorney, Agent, or Firm* — Andrew L. Salvatore, Esquire

(57) ABSTRACT

The subject invention describes a method of use of Ropinirole™ to alleviate and control menopausal symptoms in women, and in particular, hot flashes. The invention describes the use of Ropinirole as a dopamine agonist with affinity for the dopamine $D_2$, $D_3$, or $D_4$ receptors. Ropinirole may also be used to treat menopausal symptoms in conjunction with Tizanidine™ to further reduce the effects menopausal symptoms by providing a sedative and muscle relaxant effect which aids in sleep. The combination of Ropinirole and Tizanidine provides a useful new compound for treatment of menopausal symptoms that are most disruptive to the functioning in activities of daily living.

7 Claims, No Drawings

METHOD AND COMPOUND FOR TREATMENT OF MENOPAUSAL SYMPTOMS

TECHNICAL FIELD

The subject invention relates to treatments and treatment methods of menopausal symptoms including hot flashes and sleep disturbance associated with menopause. Menopause and menopausal symptoms are controlled within the body by hormones which transmit information for the production or inhibition of various molecules which act to produce menopausal symptoms. The subject invention provides for a novel combination of drugs and a new method of use which simulate the effect of naturally occurring neurotransmitters and thus aid in controlling menopausal symptoms.

BACKGROUND OF THE INVENTION

Menopause reflects the loss of function of the ovaries which affects all women at certain ages of their lifetimes. It typically begins naturally in middle age (late 40s through early 50s) over a period of time. However, menopause may occur more abruptly and earlier in certain medical conditions or when induced through surgical removal of the ovaries. The natural symptoms of menopause usually begin slowly, during a phase described as menopausal transition or perimenopause, and can be devastating. These menopausal symptoms include irregular menses, hot flashes and night sweats, sleep disruption, atrophy of reproductive tissues, increased stress, tenderness of the breast, vaginal dryness, mood changes, forgetfulness, and sometimes osteoporosis and heart disease.

One of the most prevalent symptoms is the typical "hot flash" which is a woman's perception of a sudden increase in body temperature. The hot flash is the result of vascular changes which permit rapid increased blood flow through vessels. During a hot flash, the body temperature rises rapidly and then only slowly returns to its normal body temperature.

Various methods have been used to treat menopausal symptoms, and in particular, hot flashes. Hormonal Replacement Therapy (HRT) is a form of treatment which supplements naturally occurring hormones in the body. At normal levels, estrogen and progestin counter the effects of other hormones, such as luteinizing hormone (LH) and follicle stimulating hormone (FSH). During menopause, as estrogen and progestin levels are reduced, and levels of LH and FSH are found at high levels and menopausal symptoms become more apparent. [http://en.wikipedia.org/wiki/Menopause (accessed Feb. 2, 2012)]. HRT treatment aims to supplement levels of estrogen and progestin to reduce levels of LH and FSH and thus reduce menopausal symptoms.

Increased levels of estrogen, though, create a risk of a number of other health risks including cancer, heart attack, and strokes. [Decline in use of hormone therapy among postmenopausal women in the United Kingdom, Menopause 14 (3 Pt 1): 462-7; Differences in menopausal hormone therapy use among women in Germany between 1998 and 2003, BMC Womens Health 7: 19; Prescribing of hormone therapy for menopause, tibolone, and bisphosphonates in women in the UK between 1991 and 2005, Eur. J. Clin. Pharmocol. 63 (9): 843-9]. Accordingly, HRT treatment may create potentially undesirable consequences far more devastating that the effects of menopausal symptoms, such as stimulating the growth of malignant cells.

Use of selective serotonin re-uptake inhibitors (SSRIs) is another method which has been used to treat menopausal symptoms. SSRIs have typically been used as antidepressants. SSRIs increase levels of serotonin by inhibiting its re-uptake into presynaptic cells. In theory, by increasing the levels of serotonin in the brain, the claimed benefits achieved as an anti-depressant, i.e. improving mood and promoting sleep, also serve to alleviate menopausal symptoms. However, the efficacy of SSRIs has been disputed. [Serotonin and Depression: A Disconnect between the Advertisements and the Scientific Literature, PLoS Medicine 2 (12): e392].

Selective Estrogen Receptor Modulators (SERMs) is another category of drugs which have been used to treat menopausal symptoms. These drugs act as agonists or antagonists to estrogen receptors throughout the body. However, it has been reported that most SERMs actually increase hot flashes. [http://en.wikipedia.org/wiki/Menopause (accessed Feb. 2, 2012). See also Menopausal Symptoms, Clin. Exp. Obstet. Gynecol. 31 (2): 123-6]. Other drugs such as anti-seizure medications (i.e., gabapentin), and blood pressure medications (i.e., clonidine), have also been used to treat menopausal symptoms. [http://en.wikipedia.org/wiki/Menopause (accessed Feb. 2, 2012)]. The mechanism of action of these agents is poorly understood, and the effectiveness of these treatments is disputed. [Gabapentin for hot flashes in 420 women with breast cancer: a randomized double-blind placebo-controlled trial, Lancet. 366(9488): 818-24; Positive efficacy data from a phase 2 trial of gabapentin extended-release in the treatment of menopausal hot flashes, Menopause, 15(6): 1225; Nonhormonal Therapies for Menopausal Hot Flashes: Systematic Review and Meta-analysis, JAMA, 295(17):2057-71].

Natural regulation of menstrual cycles is controlled by complex interactions between various hormones and hormone producing glands within the body. The hypothalamus in the brain is a primary regulator of menstrual cycles. Hormones produced by the hypothalamus in the regulation of menstrual cycles include dopamine and prolactin. Dopamine inhibits the release of prolactin, while Thyrotropin Releasing Hormone (TRH) promotes the release of prolactin. Dopamine receptors in the body may be grouped into categories producing different effects depending on the type of receptor to which dopamine binds. Receptors of groups $D_2$, $D_3$, or $D_4$ produce effects contrary to those of group $D_1$ and $D_5$. [D2 Dopamine receptor subtype mediates the inhibitory effect of dopamine on TRH-induced prolactin release from the bullfrog pituitary, Gen. Comp. Endocrinology, 168(2):287-92; Dopamine $D_1$ receptor analogues act centrally to stimulate prolactin secretion in ewes, J. Endocrinology, 137:457-64]. Dopamine binding to receptors $D_2$, $D_3$, or $D_4$ in the hypothalamus will inhibit the production of prolactin, and also inhibit the pulsatile production of Gonadotropin Releasing Hormone (GnRH) in estrogen deficient females [Regulation of Gonadotropin-Releasing Hormone (GnRH)-Receptor Gene Expression in Tilapia: Effect of GnRH and Dopamine, Biology of Reproduction, 70:1545-51]. It is the latter effect which in turn inhibits the production of LH and FSH in the pituitary gland in the estrogen deficient state of perimenopause and menopause. LH and FSH stimulate various functions in the reproductive and menstrual cycles. To the contrary, dopamine binding to the $D_1$ and $D_5$ receptors will stimulate the production of prolactin and will increase the production of GnRH thus leading to an increase in hot flashes. [D2 Dopamine receptor subtype mediates the inhibitory effect of dopamine on TRH-induced prolactin release from the bullfrog pituitary, *Gen. Comp. Endocrinology,* 168(4287-92].

LH and FSH are found at high levels during menopause. When levels of estrogen are higher, prior to menopause, estrogen provide a feedback loop which serves to limit the production of LH and FSH. However, during menopause, when levels of estrogen drop, levels of LH and FSH Increase. Studies have shown that LH and FSH act as vasodilators which increase the flow of blood throughout the vessels. The increase in the flow of blood causes symptoms of hot flashes.

Drugs which activate a receptor to produce a pharmacological response are called agonists. These drugs may mimic the effect of the naturally occurring substance. An antagonist counteracts the pharmacological effect of a drug or a naturally occurring substance. U.S. Pat. No. 7,645,750 describes the use of certain drugs in the treatment of menopausal symptoms, in particular, hot flashes. In particular, the patent describes the use of risperidone, quetiapine, clozapine, olanzapine, aripiprazole, ziprasidone, zotepine, or 9-hydrozyrisperidone as serotonin type 2A (5-HT$_{24}$) and dopamine type 2 (D$_2$) receptor antagonists. However, the efficacy of administering these drugs to treat menopausal symptoms has been disputed. [The Safety of Verlipride, *Expert Opin. Drug Saf.* 5(5):695-71]. As is discussed herein, the subject invention describes treatment with a dopamine agonist to provide relief of menopausal symptoms. Accordingly, it follows that treatment with a dopamine antagonist provides contrary results.

Ropinirole™ is a dopamine agonist manufactured by GlaxoSmithKline, Cipla, and Sun Pharmaceutical. The chemical formula for Ropinirole is 4-[2-(dipropylamino) ethyl]-1,3-dihydro-2H-indol-2-one as follows:

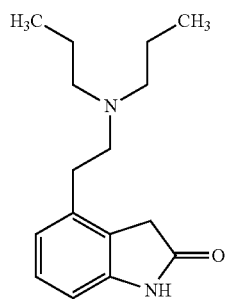

Ropinirole has typically been used in the treatment of Parkinson's disease. It has also been used to treat Restless Legs Syndrome. Ropinirole has high affinity to D$_2$, D$_3$, or D$_4$ dopamine receptors with the highest affinity for D$_2$. [Preclinical Pharmacology of Ropinirole (SK&F 101468-A) a Novel Dopamine D2 Agonist, *Pharmacology Biochemistry & Behavior* 38: 147-154]. However, Ropinirole has not previously been studied or used in the treatment of menopausal symptoms except by the inventor as discussed herein to illustrate the utility of the subject invention.

The other symptom after hot flashes that is equally, if not more, damaging to the daily functioning of a menopausal woman is sleep deprivation. Tizanidine is the molecule that can most effectively address this symptom. Tizanidine™ (a/k/a Zanaflex™), chemical formula 5-chloro-N-(4,5-dihydro-1H-imidazol-2-yl)benzo[c][1,2,5]thiadiazol-4-amine, is a drug compound which has traditionally been used as a muscle relaxant. The molecular structure of Tizanidine is as follows:

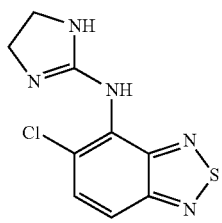 [SMILES: Clc1ccc2nsnc2c1NC1=NCCN1]

As such, it has been used in the treatment of disorders such as multiple sclerosis, spastic diplegia, back pain, and other problems related to the spine and central nervous system. [A Practical Overview Of Tizanidine Use For Spasticity Secondary To Multiple Sclerosis, Stroke, And Spinal Cord Injury, *Curr Med Res Opin* 24(4425-39]. Tizanidine is also an excellent sedative [http://en.wikipedia.org/wiki/Tizanidine (accessed Jan. 8, 2012)]. Tizanidine has not previously been considered or used in the treatment of menopausal symptoms of sleep disturbance except by the inventor as discussed herein to illustrate the benefits of the subject invention.

Given the risk of some of the current methods of treatment, and the failure of those methods to adequately treat and control menopausal symptoms such as hot flashes and sleep deprivation, there remains a need for improved means of addressing and treating these symptoms. The subject invention addresses these concerns and provides a new combination of drugs and methods of use which previously have not distinctly been shown to reduce the severity of hot flashes and menopausal symptoms of sleep disruption.

SUMMARY OF THE INVENTION

Two of the most incapacitating symptoms of menopause are hot flashes and disruption of the normal sleep pattern. Although there have been many attempts to address each of these symptoms individually, there is no singular product that addresses both problems.

The subject invention describes a novel and new use of Ropinirole to alleviate and control menopausal symptoms in women, and in particular, hot flashes. The invention describes the use of Ropinirole as a dopamine agonist with affinity for the dopamine D$_2$, D$_3$, or D$_4$ receptors. Clinical studies submitted have shown that treatment with Ropinirole significantly reduced hot flashes and menopausal symptoms. It is believed that Ropinirole reduces production of GnRH which in turn reduces production of LH and FSH. The use of Ropinirole as a menopausal symptom treatment overcomes the limitations of the prior art as it does not pose some of the significant health effects and side effects associated with HRT therapy and use of anti-depressant medication such as SSRIs. Further, the clinical trials submitted have shown the use of Ropinirole to have a much greater efficacy than traditional menopause treatments in the prior art described above.

Additionally, Tizanidine, when used in combination with Ropinirole, further reduces the effects menopausal symptoms by providing a sedative and muscle relaxant effect which aids in sleep. The muscle relaxant effect further impacts vasodilatlon which may influence the response to hot flashes. This new combination of drugs addresses problems associated with menopausal symptoms and loss of sleep in one medication. Most critically, it is safe for women who have any medical issues related to taking hormone replacement therapy, such as hormone sensitive breast cancer patients, ovarian cancer patients and uterine cancer patients, those with clotting disorders, women with a history of hypertension and those women who smoke.

DETAILED DESCRIPTION OF INVENTION

Hot flashes of menopause are vasomotor events characterized by sudden bursts of intense warmth in the chest, which may ascend to the neck and face. This feature is often accompanied by profuse sweating, skin blotching and possibly even palpitations and anxiety. Estimates suggest a prevalence of 75% in postmenopausal women, with an onset of one to two years prior to menopause and a duration of six months to five years.

Hot flashes can be particularly disruptive at night, initially causing drenching sweats followed by a sensation of cold, interrupting sleep separately from the sleep disturbance of menopause.

During the day, hot flashes can impede an affected individual's ability to function effectively with negative consequences on job performance, quality of life and self-esteem. Although generally appreciated as a condition affecting women, hot flashes can also affect as many as 75% of men following hormonal ablation therapy in the treatment of prostate cancer.

Although the precise mechanism causing hot flashes remains unknown at present, their onset occurring in concert with the withdrawal of end organ hormones, such as estrogen in the female and testosterone in the male, suggests a causal relationship. This is supported by the responsiveness of resolution of symptoms by women treated with Hormone Replacement Therapy (HRT).

Unfortunately, efforts to treat hot flashes in women with HRT, although generally successful in 80-90% of women, are now also recognized to place women with a personal or family history of breast cancer, ovarian cancer, uterine cancer, venous thromboembolism, cardiovascular disease, stroke or a positive smoking history, at increased risk.

Women who undergo rapid end organ hormonal withdrawal due to medical/surgical menopause, such those undergoing total abdominal hysterectomy, or survivors of either breast cancer or ovarian cancer subjected to hormonal blocking therapies (aromatase inhibitors to block hormone synthesis or tamoxifen to block hormone receptors), are inherently more sensitive to the development of hot flashes.

Withdrawal of end organ steroid hormones are accompanied by a predictable rise in pituitary gonadotrophins. In women there is a measureable rise in luteinizing hormone (LH) and follicle stimulating hormone (FSH). Factors contributing to this increase are not only the decline in end organ steroid hormones, but the impact of changes in other relevant molecules such as inhibin.

Efforts to control hot flashes have initially focused primarily on HRT, with the goal of restoring estrogen to suppress the hypothalamic-pituitary-gonadal axis through which the hot flashes are believed to be mediated. Due to the side effects of HRT, alternatives have been sought over the course of the past decade. Although natural supplements have been advocated, these tend to be rich in phytoestrogens, so they are predisposed to the same concerns which have dissuaded the regular use of HRT.

In contrast, with the availability of later generation dopaminergic agonists such as Ropinirole, there is now the opportunity to intervene in the putative hormonal feedback loop without the use of hormones. Just as dopamine can interfere with the release of the pituitary hormone prolactin, a dopamine agonist may also impede the release of the hypothalamic gonadotrophic hormone, GnRH. Ropinirole is a dopamine agonist with full intrinsic activity at the $D_2$ and $D_3$ dopamine receptor subtypes, binding with higher affinity at the $D_3$ than to the $D_2$ or $D_4$ receptor subtypes. It impacts the biofeedback path to control GnRH, and reduces hot flashes. The mechanism of action is postulated to be mediated through the down-regulatory role of dopamine on prolactin and gonadotropin releasing hormone, which would influence the pulsatile unbridled release of LH and FSH of menopause. Ropinirole is a well-tolerated medication, with an excellent safety profile.

Tizanidine is a muscle relaxant which further aids in the reduction of hot flashes. Tizanidine is also used as an excellent sedative. In combination with Ropinirole, these drugs effectively treat problems associated with menopausal symptoms and loss of sleep in one medication. In addition, these drugs are safe for women who have any medical issues related to taking hormone replacement therapy, such as hormone sensitive breast cancer patients, ovarian cancer patients and uterine cancer patients, those with clotting disorders, women with a history of hypertension and those women who smoke.

The invention contemplates that various forms may be used to administer this combination of Ropinirole and Tizanidine. For instance, these compounds may be administered in a single pill where separate components are combined Into sections of the pill or combined throughout a single pill. These compounds may also be administered in a liquid format to be administered orally or intravenously. The compounds may also be administered in the form of a transdermal patch to be worn on the skin. Another method of drug administration may be inhalation of the drug compounds. The invention also contemplates that these compounds may be administered by other known means of administering drug compounds.

Additionally, the invention contemplates that other chemical compounds having the properties of Ropinirole or Tizanidine and producing the same effects may also be used in place of Ropinirole or Tizanidine. For instance, compounds acting as a dopamine agonist and binding at the $D_2$, $D_3$, or $D_4$ dopamine receptors may also be used for relief of menopausal symptoms, and in particular, hot flashes. Compounds having a sedative effect may also be used to provide relief of menopausal symptoms. These compounds may also be used in combination to provide effective relief from menopausal symptoms.

Clinical Studies

The efficacy of Ropinirole alone to treat menopausal symptoms has been demonstrated through studies of treatments of four patients with these symptoms. Relief from menopausal symptoms was further enhanced through treatment with Tizanidine. The patients were treated by escalating the dose of Ropinirole to 4 mg, testing the hypothesis of a dopaminergically regulated pathway within the central nervous system which impacts hot flashes. The dopaminergic agonist Ropinirole was escalated from an initial dose of 0.25 mg to a final dose of 4 mg at bedtime without side effects and with the dramatic shutdown of previously intolerable hot flashes of menopause.

Case #1

JK, a 58 year old woman, began experiencing symptoms of insomnia and had initially been placed on low dose Hormone Replacement Therapy (HRT) without benefit on her sleep cycle. Despite two changes in dose and formulation of HRT, no significant benefit in sleep cycle was realized. Neither were efforts to treat her sleep problems with standard sedative hypnotics such as zolpidem, zaleplon, temazepam or clonazepam. Hot flashes then began, and became both more frequent and more intense. These were characterized by severe flushing of the face and upper chest with drenching sweats. Each hot flash would typically last 30-90 seconds and were accompanied by an intense sensation of heat. The hot flash would then rapidly subside with a sense of being chilled, reflecting the normal physiologic function of evaporation of perspiration. A period of 10 to 90 minutes would elapse before the next hot flash would occur, both during the daytime and throughout the night. It was common for there to be between 20 to 30, and as many as 40 hot flashes over the course of a day at their peak in frequency, although not all would be of the same intensity.

Treatment was initiated with Tizanidine, a non-selective alpha-2-adrenergic agonist, for the purpose of providing a sleep aide. Tizanidine is available as a scored 4 mg tablet that can easily be broken into four 1 mg portions. Therefore, the initial dose provided was 1 mg at bedtime, and the dose was raised as needed, every fourth day, to a maximum of 8 mg, if needed, usually at bedtime. However, if the maximum of 8 mg was not taken at bedtime, the patient was permitted to use up to the remaining amount of Tizanidine, but not more than a total of 8 mg for the night if she awoke during the night and found that she could not fall back to sleep. This was not necessary, and once asleep, she was able to sleep through the night waking infrequently but rapidly falling back to sleep.

Safety monitoring included making certain there were no issues with liver function, low blood pressure or unusual dreams as this was accomplished. Tizanidine could, if needed, be dosed again during the night without causing a morning "hangover" effect providing there was a four hour sleep window available.

HRT was not an option for controlling her hot flashes since this woman had been diagnosed with hormone receptor positive breast cancer. She had additional challenges in the potential treatment of hot flashes because of the history of breast cancer. This was in part because she had received chemotherapy which caused a peripheral neuropathy. Consequently, the hot flashes she experienced were perceived with even greater intensity because the overwhelming sense of rising body heat was in direct contrast to the constant freezing cold sensation of the neuropathy felt in both feet. In addition, she was receiving an aromatase inhibitor (anastrozole, 1 mg daily), a medication to block the production of estrogen and progesterone, in effect, anti-HRT. This further exacerbated the hot flashes into "super" hot flashes, a known side effect of this type of medication. For her, the "super" hot flashes were beyond the intensity of her previously experienced menopausal hot flashes. These hot flashes were crippling. They prevented her from functioning normally, required that she bring changes of underwear and clothing to work, interrupted her sleep and interfered with her ability to function in her normal activities of daily living. They impacted her safety and the safety of others as well, regarding her ability to effectively drive and accurately perform her job duties.

Other medication alternatives reported in the medical literature which had partial success in reducing hot flash frequency and severity by as much as 50% were evaluated by titrating to the doses reported, and maintained at those doses for at least a two week trial. These included clonidine at a dose up to 0.4 mg, gabapentin at a dose of up to 1800 mg and venflaxamine at a dose of up to 300 mg. However, these were not satisfactory in reducing hot flashes by more than 25% in this individual. Therefore, following the unsuccessful trials with these agents the focus was switched to a trial with a novel agent, Ropinirole, a dopamine agonist.

With Ropinirole, the goal has been directed at regulating GnRH, and controlling the unsuppressed LH pulses characteristic of menopause, through the action on $D_2$ and $D_3$ receptors within the hypothalamus. Prior ineffective dopamine agonists that have been used for this purpose have had opposite actions on these molecules because they worked on the $D_1$ and $D_5$ receptors. The responses of the $D_1$ and $D_5$ receptors vs. the $D_2$, $D_3$ and $D_4$ receptors are diametrically opposed.

Ropinirole titration was initiated with 0.25 mg at bedtime, and if tolerated, by escalating the dose by 0.25 mg every fourth day to a maximum of 1 mg (i.e., 0.25 mg, 0.50 mg, 0.75 mg, 1 mg), until there was reduction in both the frequency and severity of hot flashes. If higher doses were needed, then both 1 mg, or later 2 mg and both 1 and 2 mg Ropinirole tablets were used along with the continued titration by 0.25 mg steps every fourth day until a maximum of 4 mg was reached. Higher Ropinirole doses were not needed to accomplish clinical suppression of the hot flashes in this woman, but were not tested either due to a greater likelihood of side effects such as nausea, hallucinations or jitteriness.

With this protocol it was possible to provide aide to allow this patient to fall asleep within 15 to 20 minutes, rather than tossing and turning for up to two hours before falling asleep. In addition, this patient was able to sleep through the night for seven to eight hours on this treatment, while without treatment she had been awakening anywhere from two to three times per hour once she did fall asleep.

The combination of Ropinirole and Tizanidine represented a new combination that provided aide in falling asleep, staying asleep and providing significant additional relief by completely eliminating the frequency and severity of hot flashes that this patient had experienced prior to treatment. This was a highly significant and dramatically notable improvement compared to any prior option available. Ropinirole was shown to reduce hot flashes as a dopamine agonist on the $D_2$, $D_3$ and $D_4$ receptors. The new combination of Ropinirole and Tizanidine was additionally effective in totally eliminating the most severe form of hot flashes, with the most intense vasomotor symptoms. It completely stopped the frequency and intensity of these symptoms. When the dose of Ropinirole was removed, the symptoms returned. When the Ropinirole was re-administered at 4 mg, the hot flashes once again disappeared.

Case #2

JM is a 52 year old woman with multiple sclerosis (MS) for 26 years. She had been experiencing difficulty with vision, inability to walk due to spinal symptoms, severe neurogenic bladder with incontinence, fatigue and multiple hot flashes throughout the day causing severe sweats and a sensation of heat overcoming her body. Ironically, with the sensation of heat there was an overwhelming sense of weakness and fatigue. This possibly reflected what is known as the "pseudoexacerbation" phenomenon in MS. Central nervous system (CNS) nerve fibers that already are physically damaged, but somewhat physiologically compensated, can lose their ability to compensate as body temperature rises. The function of these nerve fibers can improve once again as body temperature cools.

Patient JM is extremely temperature sensitive and wears a cooling vest to remain on the cool side for this very purpose. Prior to treatment with Ropinirole for the regulation of her hot flashes, IM had been experiencing anywhere from 15-20 hot flashes per day, with severe flushing of the face and chest and associated weakness. She attempted to cool herself with a hand held, battery operated fan and by drinking ice cold liquids. While that effort provided some improvement of symptoms by shortening the duration of her hot flash associated weakness, it did not prevent the recurrent episodes. Hormone Replacement Therapy (HRT) was not an acceptable option for her due to her high risk profile for Deep Vein Thrombosis (DVT) because of her immobility due to paralysis from the MS, and her smoking history.

She was using Tizanidine for treatment of spasticity and the dose was adjusted to provide 8 mg at bedtime to facilitate sleep, which it did. In addition, she was titrated up to a Ropinirole dose of 4 mg daily at bedtime which totally eliminated the vasomotor symptoms (hot flashes) without side effects. In addition, there was also resolution of the MS pseudoexacerbation phenomenon. The combination of these two agents provided a new product that aided her falling asleep, staying asleep and completely eliminated her hot flashes of menopause, in a circumstance where HRT was contraindicated due to high risk of vascular complications from immobility and smoking (DVT).

Case #3

DH is a 53 year old woman with multiple peripheral nerve injuries and diabetes. She entered menopause two years ago and developed the menopausal symptom of hot flashes with a frequency of 15-20 hot flashes per day, with each one lasting 15-30 seconds in duration. There was flushing and reddening of the face and the chest, with associated beading of sweat, during these hot flashes and they interfered with her ability to obtain a full night of normal sleep. She had been able to fall asleep with the use of sedative hypnotic medication, temazepam, even prior to the onset of the hot flashes.

After the onset of the hot flashes she noted difficulty sleeping throughout the night because of drenching night sweats associated with the hot flashes after which she would feel very cold. HRT was not an acceptable form of treatment due to metabolic issues with the control of her diabetes. She then received the combination of both Tizanidine, titrated up to 8 mg at bedtime, and Ropinirole, which was also titrated as with the other patients. Her sleep improved and her hot flashes completely resolved at a dose of 4 mg at bedtime with no untoward side effects.

Cessation of the hot flashes, combined with uninterrupted sleep not only leads to a more productive work day, but a safer day as well, regarding such activities as operating an automobile, where alertness is imperative. Her diabetes remained under excellent control.

Case #4

PW is a 48 year old woman with a chronic neuropathic pain disorder who entered menopause at a younger age than most, but developed hot flashes with drenching night sweats as significant symptoms like most. The hot flashes were associated with facial flushing and flushing of the chest. These episodes lasted 15-30 seconds each and would occur 10-15 times per day. She already was under treatment with clonidine, gabapentin and venflaxamine for her neuropathic pain and associated depression, and developed these hot flash symptoms despite those medications. Hormone Replacement Therapy (HRT) was contraindicated because of the potential for worsening her depression. Tizanidine 4 mg was titrated for sleep to 8 mg at bedtime, and treatment with Ropinirole was initiated and titrated to 4 mg at bedtime. She slept and on the Ropinirole 4 mg at bedtime she had complete resolution of the frequency and severity of the hot flashes without untoward side effects. She previously had manifested irritability and difficult concentrating which seemed to improve as the hot flashes abated and sleep improved.

The combination of these two agents represents a new combination that provides aide in falling asleep, staying asleep and providing significant relief by completely eliminating the frequency and severity of hot flashes which were resistant to other medication described as potentially useful in the medical literature. HRT would not have been an acceptable alternative for this patient because of the probability of it having a negative impact on her already altered mood state associated with her pain disorder. This new product was effective in totally eliminating her intense vasomotor symptoms (hot flashes), and improving her ability to sleep.

Two of the most incapacitating symptoms of menopause are hot flashes and disruption of the normal sleep pattern. Although there have been many attempts to address each of these symptoms individually, treatment methods thus far do not adequately resolved symptoms, and many have also created additional health risks. Further, no singular product has addressed both of these symptoms.

The subject invention describes a novel and new use of Ropinirole to alleviate and control menopausal symptoms in women, and in particular, hot flashes. As a dopamine agonist, Ropinirole is believed to bind to the $D_2$, $D_3$, or $D_4$ receptors, particularly at the $D_3$ site. This affinity inhibits production of GnRH which reduces production of LH and FSH in the pituitary. LH and FSH are vasodilators, and lower levels of LH and FSH result in reduced incidence of hot flashes.

Clinical studies have shown that treatment with Ropinirole significantly reduced hot flashes and menopausal symptoms. The use of Ropinirole as a menopausal symptom treatment overcomes the limitations of the prior art as it does not pose some of the significant health effects and side effects associated with other treatment methods. Further, clinical studies have shown the use of Ropinirole to have a much greater efficacy than traditional menopause treatments.

The combination of these two agents, Tizanidine and Ropinirole, represents a new product that provides aide in falling asleep and staying asleep and provides complete elimination of hot flashes in experimental studies.

The invention has been disclosed in terms of preferred embodiments which fulfill all of the objects of the present invention and overcome the limitations of the prior art. Various changes, modifications, and alterations from the teachings of the present invention may be contemplated by those skilled in the art without departing from the intended spirit and scope thereof. It is intended that the present invention only be limited by the terms of the appended claims.

What is claimed is:

1. A composition for treatment of menopausal symptoms, comprising: a substance that is a dopamine agonist capable of binding to $D_2$, $D_3$ or $D_4$ dopamine receptors, and a substance having sedative effects, wherein the dopamine agonist is Ropinirole and the compound having sedative effects is Tizanidine, and wherein the composition is provided as a unit dosage in an amount of Ropinirole in a range from 0.25 mg to 4 mg per day, and in an amount of Tizanidine in a range from 1 mg to 8 mg per day.

2. A composition as set forth in claim 1 wherein compound A and compound B comprise a pill form.

3. A composition as set forth in claim 2 wherein compound A and compound B are separately placed within the pill.

4. A composition as set forth in claim 2 wherein compound A and compound B are combined within the pill.

5. A compound composition as set forth in claim 1 comprising a form which is capable of administration to an individual orally as a liquid.

6. A composition as set forth in claim 1 comprising a form which is capable of administration to an individual intravenously as a liquid.

7. A composition as set forth in claim 1 comprising a form which is capable of administration to an individual by inhalation.

\* \* \* \* \*